United States Patent [19]

Anaissie et al.

[11] Patent Number: 4,999,199

[45] Date of Patent: Mar. 12, 1991

[54] PHARMACEUTICAL FORMULATIONS: LIPOSOMES INCORPORATING AROMATIC POLYENE ANTIBIOTICS

[75] Inventors: Elias J. Anaissie; Georgios Samonis, both of Houston, Tex.; Hans Krause, Worms-Horchheim, Fed. Rep. of Germany; Gerald P. Bodey, Houston, Tex.

[73] Assignee: Board of Regents, The University of Texas System, Austin, Tex.

[21] Appl. No.: 269,638

[22] Filed: Nov. 10, 1988

[51] Int. Cl.⁵ .............................................. A61K 37/22
[52] U.S. Cl. .................................... 424/450; 424/417; 514/37; 264/4.1; 264/4.3; 264/4.6
[58] Field of Search .................. 424/450, 417; 514/37; 264/4.1, 4.3, 4.6

[56] References Cited

U.S. PATENT DOCUMENTS

| 4,536,494 | 8/1985 | Carter ..................................... 514/31 |
| 4,663,167 | 5/1987 | Lopez-Berestein et al. .......... 514/37 |
| 4,812,312 | 3/1989 | Lopez-Berestein .................. 424/450 |

FOREIGN PATENT DOCUMENTS

| 87307221.9 | 8/1987 | European Pat. Off. . |
| US86/01881 | 9/1986 | PCT Int'l Appl. . |
| US88/03831 | 10/1988 | PCT Int'l Appl. . |

OTHER PUBLICATIONS

Advances in Lipid Research, vol. 14, 1976, pp. 127–171.
International Search Report, PCT/US 89/04650, mailed Feb. 28, 1990.
Kinsky, "Nystatin Binding by Protoplasts and a Particulate Fraction of Neurospora crassa, and a Basis for the Selective Toxicity of Polyene Antifungal Antibiotics", Proc. Natl. Acad. Sci U.S.A., vol. 48 (1962) 1049–1056.
Weissmann et al., "The Action of Polyene Antibiotics on Phospholipid-Cholesterol Structures", J. Biol. Chem., vol. 242, No. 4 (1967) 616–625.
Goth, "Antifungal Antibiotics", Medical Pharmacology, Ninth Edition, The C. V. Mosby Company, St. Louis (1978) 604–607.
Goodman et al., "II. Antifungal Agents", The Pharmacological Basis of Therapeutics, Fifth Edition, Mac-Miller Publishing Co., Inc., New York (1975) 1235–1238.
Drouhet et al., "Evolution of Antifungal Agents: Past, Present, and Future", Rev. Infect. Dis., vol. 9 (1987) S4–S14.
Hamilton-Miller, "Chemistry and Biology of the Polyene Macrolide Antibiotics", Bactiol. Rev., vol. 37, No. 2, (1973) 166–196.
New, "Antileishmanial Activity of Amphotericin and Other Antifungal Agents Entrapped in Liposomes", J. Antimicrobial Chemother., vol. 8 (1981) 371–381.
Taylor et al., "Amphotericin B in Liposomes: A Novel Therapy for Histoplasmosis", Am. Rev. Respir. Dis., vol. 125 (1982) 610–611.
Graybill et al., "Treatment of Murine Cryptococcosis with Liposome-Associated Amphotericin B", J. Infect. Dis., vol. 145, No. 5 (1982) 748–752.
Tremblay et al., "Comparative Efficacy of Amphotericin B (AMB) and Liposomal AMB (Lip-AMB) in Systemic Candidiasis in Mice", Abstr. 1983 ICAAC, No. 755 (1983) 222.
Graybill et al., "Treatment of Coccidioidomycosis (Coccy) in Primates Using Liposome Associated Amphotericin B (Lipo-AMB)", Abstr. ICCAC No. 492 (1982) 152.
Lopez-Berestein et al., "Liposome-Encapsulated Amphotericin B for Treatment of Disseminated Candidiasis in Neutropenic Mice", J. Infect. Dis. vol. 150 (1984) 278–283.
Lopez-Berestein et al., "Liposomal Amphotericin B for the Treatment of Systemic Fungal Infections in Patients with Cancer: A Preliminary Study", J. Infect. Dis. vol. 151, No. 4 (1985) 704–710.
Dutcher, "Polyene Antibiotics", Kirk-Othmer Encyclopedia of Chemical Technology, vol. 16 (1968) 133–143.
Pansy et al., Comparative Chemotherapeutic Activities of Heptaene Macrolide Antifungal Antibiotics in Experimental Candidiasis, J. Antibiot., vol. 25 (1972) 405–408.

(List continued on next page.)

Primary Examiner—Merrell C. Cashion, Jr.
Assistant Examiner—P. L. Prater
Attorney, Agent, or Firm—Arnold, White & Durkee

[57] ABSTRACT

The present invention involves a pharmaceutical formulation comprising a liposome having a therapeutically effective concentration of an aromatic polyene macrolide antibiotic. The aromatic polyene macrolide antibiotic usable in the practice of the present invention is selected from the group consisting of candicidin, hamycin, aurefungin, ascosin, ayfattin, azacolutin, DJ400-B, trichomycin, levorin, heptamycin, candimycin or perimycin. The most preferred aromatic polyene macrolide antibiotic is candicidin. An important aspect of the present invention is a method for treating disseminated fungal infection in an animal comprising administering to an animal such as a human a pharmaceutical formulation comprising a liposome having a therapeutically effective amount of aromatic polyene macrolide antibiotic as described above. The preferred method of such administering is parenteral and the therapeutically effective amount is between about 1 mg/kg body weight and about 20 mg/kg body weight, more preferably between about 2.5 mg/kg body weight and about 6 mg/kg body weight. The parenteral administration is intravenous, intraarterial, subcutaneous, intramuscular, intralymphatic, intraperitoneal or intrapleural. The microorganisms which may be treated by the methods of the present invention comprise C. albicans, C. tropicalis, C. neoformans, aspergillus, cryptococcus, phycomycetes, fusarium, or trichosporin.

35 Claims, No Drawings

OTHER PUBLICATIONS

Waksman et al., "Candicidin and Other Polyenic Antifungal Antibiotics", Bull. World Health Org., vol. 33 (1965) 219–226.

Singh et al., "Parenteral Emulsions as Drug Carrier Systems", J. Parenteral Sci. Tech., vol. 40 (1986) 34–41.

Dolce et al., "Systemic Clearance of Amphotericin B Delivered in a Parenteral Lipid Emulsion to Rats", Clin. Pharmacol. Ther., vol. 41 (1987) 166.

Kahn et al., "The Pharmacokinetics of Amphotericin B in an Emulsion Formulation", Clin. Pharmacol. Ther., vol. 41 (1987) 194.

Shadomy et al., "Laboratory Studies with Antifungal Agents: Susceptability Tests and Bioassays", Manual of Clinical Micrology, Washington, D.C. American Society for Microbiology (1985) 991–999.

Bolard et al., "Effect of Surface Curvature on the Interaction of Single Lamellar Phospholipid Vesicles with Aromatic and Non-Aromatic Heptaene Antibiotics (Vacidin A and Amphotericin B)", Biochem. Pharmocol., vol. 33 (1984) 3675–3680.

Witzke et al. "Dissociation Kinetics and Equilibrium Binding Properties of Polyene Antibiotic Complexes with Phosphatidylcholine/Sterol Vesicles", Biochem., vol. 23 (1984) 1668–1674.

Lopez–Berestein, "Liposomal Amphotericin B in the Treatment of Fungal Infections", Ann. Int. Med., vol. 105 (1986) 130–131.

Lopez–Berestein et al., "Effects of Sterols on the Therapeutic Efficacy of Liposomal Amphotericin B and Murine Candidiasis", Can. Drug Delivery, vol. I (1983) 37–42.

PHARMACEUTICAL FORMULATIONS: LIPOSOMES INCORPORATING AROMATIC POLYENE ANTIBIOTICS

BACKGROUND OF THE INVENTION

1. Field of the Invention

The present invention relates to improved pharmaceutical formulations comprising liposomes incorporating aromatic polyene antibiotics, and the use of these formulations in the treatment of fungal disease. Particular aromatic polyene antifungals which are advantageously employed in the practice of the invention include candicidin and hamycin, both having aromatic moieties such as p-aminoacetophenone incorporated into particular polyene heptaene macrolide structures. The preparation of aromatic polyene antibiotic-containing liposomes suitable for parenteral administration is disclosed.

2. Description of the Related Art

The polyenes, in general, are macrolide antibiotics that have selectivity for inhibiting organisms whose membranes contain sterols. It is believed that their activity is due to the binding of the drug to cell membrane sterols, resulting in a change in membrane permeability. This altered membrane structure permits the leakage of small molecules, and thus disrupts cellular homeostatic mechanisms (1,2). Moreover, in that the polyenes likely function by sterol binding, it is not surprising that microorganism resistance to polyene action is typically a function of its binding affinity for the particular sterol of the microorganism. Typical uses for conventional polyenes such as nystatin and amphotericin B include treatment of fungal diseases such as those resulting from Candida infections (e.g., C. albicans and C. tropicalis) as well as a variety of other diseases such as histoplasmosis, coccidioidomycosis, systemic sporotrichosis, aspergillosis, mucormycosis, chromablastomycosis, blastomycosis and cryptococcosis (3,4).

The foregoing diseases, in general, are often characterized as "opportunistic infections" in that their incidence tends to coincide with one or more "opportunistic" changes with physical state of the host. For example, the incidence of fungal infections tends to dramatically increase in the case of the immunocompromised individual, such as a patient having AIDS or undergoing cancer treatment. Thus, the polyene antibiotics have become important adjuncts in the treatment of certain opportunistic infections in individuals afflicted with AIDS or cancer. Unfortunately, the generally poor physical state of AIDS patients and others seriously ill with fungal related infections, coupled with the serious toxicities associated with macrolide polyene use, renders the use of drugs such as amphotericin B in these patients difficult at best to manage.

Although amphotericin B formulations, as well as those other non-aromatic polyene macrolides, remain of principal importance in the management of fungal disease, their overall usefulness is typically limited by the appearance of untoward effects often associated with systemic application. For example, upon parenteral administration using conventional formulations a large number and variety of untoward effects may be associated with amphotericin B is use. These toxicities include a range of symptoms, from the appearance of hypersensitivity reactions such as anaphylaxis or convulsions on occasion, to irritative and toxic effects, even acute hepatic failure (4). In general, the major cause for concern is due to the occurrence of nephrotoxicity: over 80% of persons given amphotericin B develop decreased renal function and abnormal urine sediment, evidence of toxic hepatic cell degeneration (4).

Coupled with the toxicity problems of polyene macrolide therapy is the very high degree of failure in immunosuppressed patients (5). This failure is thought to be mainly due to the immunosuppressed state of the patient, as well as the inability to deliver higher quantities of the drug. In short, the polyene macrolides typically exhibit a very poor therapeutic index or "margin of safety" when administered parenterally in the treatment of fungal disease.

The "therapeutic index" of a drug is intended to represent the ratio of the upper dosage limit of a drug that will give a certain level of toxicity (e.g., $LD_{50}$, maximum tolerated dose MTD), over some minimum level of biologic activity (e.g., minimum inhibitory concentration, MIC). The polyenes, unfortunately, tend to exhibit toxicities at levels not far removed from therapeutic levels, and this limitation represents an important problem.

One class of polyene antibiotics which has shown considerable antifungal activity in in vitro susceptibility tests are polyenes whose structure include aromatic groups (5-9). These aromatic-containing polyenes are exemplified by agents such as hamycin, candicidin, aurefungin, ascosin, ayfattin, azacolutin, DJ400-B, trichomycin, levorin, heptamycin, candimycin and perimycin, whose structures include aromatic groups such as p-aminoacetophenone or N-methyl-p-aminoacetophenone, which are attached to a macrolide backbone (6). Unfortunately, although these agents are highly active in vitro, they have yet to find utility in the clinical management of disease due to both their highly toxic nature as well as their poor solubility. In short, although the aromatic polyene antibiotic exhibit very high and broad spectrum antifungal activity (e.g., measured in terms of MICs against various fungal species), even at very low doses of activity, these agents tend to be toxic. In addition, the aromatic polyene antibiotics present other particular problems in terms of water insolubility, which further renders their use difficult and impractical.

The polyene antifungals are the most potent antifungal antibiotics. Amphotericin B is the only commercially available parenteral polyene and is the most important drug for the treatment of serious fungal infections (1). This drug is very toxic and is unlikely to cure fungal infections in severely immunosuppressed patients (2). Candicidin is a polyene antifungal available only for the topical treatment of superficial fungal infections. No parenteral formulation is available for the therapy of deep seated mycoses, because the drug is totally water insoluble and very toxic. Candicidin however has an aromatic moiety that is believed to confer to this antibiotic a much better antifungal activity than amphotericin B or other polyenes that lack this aromatic moiety in their structure. Many in vitro susceptibility experiments conducted in various laboratories, including those of the present inventors, indicate that candicidin has a much higher antifungal activity than amphotericin B against various fungi. It is therefore believed, that if a safe parenteral formulation of candicidin would be available, many of the therapeutic failures with amphotericin B could be avoided. Of note, candicidin has been given orally (without any toxicity) to humans in this country.

Accordingly, there is currently a need for improved pharmaceutical formulations particularly suited for the treatment of fungal disease. These formulations should address one or more of the disadvantages associated with previous formulations. There is, in particular, the need for formulations which exhibit broader therapeutic indexes, including lower minimum effective doses, or higher toxic doses, or both. Moreover, there is a need for safe, parenteral formulations having a sufficiently broad spectrum and/or high degree of efficacy of antifungal activity. These properties would render them particularly desirable for use in treatment of immunocompromised individuals.

It has recently been shown that the encapsulation of certain drugs in liposomes before administration to the patient can markedly alter the pharmacokinetics, tissue distribution, metabolism and therapeutic efficacy of these compounds. Liposomes may be defined as lipid vesicles which are formed spontaneously on addition of an aqueous solution to a dry lipid film. Further, the distribution and pharmacokinetics of these drugs can be modified by altering the lipid composition, size, charge and membrane fluidity of the liposome in which they are encapsulated.

Liposomes have been used as carriers of amphotericin B for treatment of murine leishmaniasis, histoplasmosis, cryptococosis and candidiasis. Liposome-encapsulated amphotericin B has also been used for treatment of coccidioidomycosis in the Japanese macaque.

It has been demonstrated that liposome-encapsulated amphotericin B (AmpB) may be used to treat experimental murine candidiasis and in the treatment of fungal infections in patients with leukemia and lymphoma.

SUMMARY OF THE INVENTION

The present invention involves a pharmaceutical formulation comprising a liposome having a therapeutically effective concentration of an aromatic polyene macrolide antibiotic. The aromatic polyene macrolide antibiotic usable in the practice of the present invention is selected from the group consisting of candicidin, hamycin, aurefungin, ascosin, ayfattin, azacolutin, DJ400-B, trichomycin, levorin, heptamycin, candimycin or perimycin. The most preferred aromatic polyene macrolide antibiotic is candicidin.

The preferred liposomes of the present invention for incorporation of aromatic polyene macrolide antibiotic comprise phospholipids and are stable multilamellar vesicles which may include a sterol such as cholesterol. The phospholipids are preferably one or more of phosphomonoglyceride, phosphatidic acid and sphingolipid such as phosphatidylcholine, phosphatidylserine, phosphatidylglycerol, sphingomyelin or phosphatidic acid. Preferable phospholipids are one or more of dimyristoylphosphatidylcholine, dimyristoylphosphatidylglycerol, phosphatidylcholine and phosphatidylglycerol. More preferably the liposomal phospholipids consist essentially of dimyristoylphosphatidylcholine and dimyristoylphosphatidylglycerol. The dimyristoylphosphatidycholine and dimyristoylphosphatidylglycerol in a preferred ratio of between about 1 to 10 and about 10 to 1, most preferably about 7:3.

An important aspect of the present invention is a method for treating disseminated fungal infection in an animal comprising administering to an animal such as a human a pharmaceutical formulation comprising a liposome having a therapeutically effective amount of aromatic polyene macrolide antibiotic as described above. The preferred method of such administering is parenteral and the therapeutically effective amount is between about 1 mg/kg body weight and about 10 mg/kg body weight, more preferably between about 2.5 mg/kg body weight and about 6 mg/kg body weight. The parenteral administration is intravenous, intraarterial, subcutaneous, intramuscular, intralymphatic, intraperitoneal or intrapleural. The microorganisms which may be treated by the methods of the present invention comprise *C. albicans, C. tropicalis*, other Candida spp., *Cryptococcus neoformans*, aspergillus, zygomycetes, fusarium, or trichosporon.

It is an overall object of the present invention to address one or more of the foregoing deficiencies in the art by providing improved pharmaceutical formulations for use in antifungal therapy.

It is a more particular object of the invention to provide pharmaceutical formulations incorporating highly active antifungal agents in a form suitable for systemic application, e.g., by parenteral routes.

It is a further object of the present invention to provide formulations particularly suited for use in the treatment of highly sensitive or, alternatively, immuno-suppressed individuals, for example, formulations incorporating little or no toxic reagents such as co-solubilizing agents.

It is a still further object of the invention to provide a safe means for antifungal treatment using the highly effective hamycin or candicidin, yet lessening or avoiding the seriousness of toxicities associated with these agents.

Accordingly, the present invention is concerned in a general sense with the provision of pharmaceutical formulations which comprise liposomes having incorporated therapeutically effective concentrations of an aromatic polyene antibiotic. It has been found that liposomes formulated to include one of this particular class of polyene, serve the dual purpose of rendering safe a drug that would otherwise be unavailable, and allowing he administration of higher doses of an already more efficacious agent. The invention thus arises in part out of the discovery that the aromatic polyenes can be rendered surprisingly more tolerable, with virtually no loss in activity, by formulation into liposomes.

The polyene antibiotics employed in connection with the present invention are aromatic polyenes and includes in a general sense, those macrolide polyenes incorporating aromatic structures such as p-aminoacetophenone and N-methyl-p-aminoacetophenone groups into their macrolide structures. In more particular embodiments, structures of the invention include aromatic moiety-containing polyene antibiotics such as candicidin and hamycin, these being generally preferred.

The liposomal preparations of the present invention are believed to exhibit substantial improvement in a variety of pharmacologic parameters over other antifungal parenteral compositions. For example, the high fat solubility found to be associated with the aromatic polyenes allows preparation of concentrated formulations in multilamellar liposomes without the need for co-solubilizing agents. Co-solubilizing agents such as deoxycholate, polysorbate, polyethylene-glycol, Tween 80 and the like, are required where higher concentrations of even non-aromatic containing polyenes, such as amphotericin B or nystatin at drug concentrations greater than about 1 to 2 mg/ml emulsion are required for administration. Co-solubilizing agents such as deoxycholate are a likely source of toxicity associated with previous compositions.

Accordingly, in certain embodiments the invention is concerned with the preparation and use of aromatic polyene containing liposomes which are substantially or essentially free of toxic amounts of one or more such co-solubilizing agents. Particularly preferred are high concentration liposomes which are essentially free of deoxycholate (a particularly likely source of toxicity).

The formulations of the invention can be prepared in a wide range of therapeutically effective concentrations, for use in a variety of differing applications. Typically, one will desire to prepare and employ liposomes incorporating aromatic polyene antibiotics at concentrations ranging from as low as about 100 ug (microgram)/ml up to concentrations as high as 2.0 mg/ml of emulsion, likely even higher where desired, depending on the application envisioned. Thus, for application in connection with treatment where very high dosages are required, one will generally prefer to prepare formulations having polyene concentrations, for example, ranging from 1.0 mg/ml up to 2.0 mg/ml, or more typically, 1.5 mg/ml. This allows the ready attainment of liposomes having very high antifungal drug concentrations previously not obtainable or only obtainable upon the addition of potentially toxic co-solubilizing agents. When one additionally considers the effective dosages attainable, the advantages of the invention become even more apparent.

It is believed by the present inventors that the liposomes of the present invention will be effective in the treatment of virtually all commonly encountered fungal disorders. These include, but are not limited to, infection due to *C. albicans, C. tropicalis*, and other candidal strains, as well as a wide variety of non-candidal fungal infections such as aspergillus species, cryptococcus, zygomycetes, fusarium species, trichosporon species and other fungal infections. It is believed that a particular advantage of the invention will likely be found in connection with the treatment of mold infections.

In the treatment of most disorders, for example, Candida and Aspergillus, it will be generally necessary to parenterally administer on the order of about 0.6 mg/kg of candicidin, or 0.6 mg/kg of hamycin, one time a day. For more serious infection such as Candida, Aspergillus or cryptococcus, as in the case of the treatment of immuno-compromised individuals, one will generally desire to employ even higher dosages, for example, on the order of about 1 to about 5 mg/kg/day.

In further aspects, the invention is directed to a method of preparing pharmaceutical formulations, e.g., for use in the treatment of fungal disease. The method including generally the steps of (a) selecting an aromatic polyene antibiotic; (b) dissolving the antibiotic in an appropriate solvent; (c) filtering the solvent containing the dissolved antibiotic to remove impurities; and (d) mixing liposome-forming lipids or phospholipids having a therapeutically effective concentration of the aromatic polyene. In preferred aspects, the formulations are prepared in a manner to provide liposomes free of co-solubilizing agents.

DETAILED DESCRIPTION OF THE PREFERRED EMBODIMENTS

The present invention is thus concerned with the preparation and use of antibiotic formulations having particularly desirable properties, surprisingly improved in various respects in comparison to other formulations used in antifungal therapy. A particular purpose of the invention is to enable the preparation and development of safe parenteral formulations incorporating aromatic moiety-containing polyene antibiotics, exemplified by candicidin and hamycin, perhaps the most potent antifungal drugs known (5, 6, 14, 15, 16).

One of the particular advantages of formulations of the present invention is believed to be a surprising improvement in the therapeutic index of the drug which is the result of a significant improvement in terms of toxic doses versus effective doses. Thus, significant improvements in the pharmacologic properties of aromatic polyenes are observed by employing antibiotics in formulations in accordance herewith. It is proposed that these formulations exhibit improvements to a greater degree than one could have predicted from similar knowledge relating to non-aromatic polyenes such as amphotericin B or nystatin (see, e.g., 17–21).

It will be appreciated by those of skill in the art that the actual preferred dosage of aromatic polyene antibiotic employed in the formulation of this invention will vary according to the particular aromatic polyene being used, the mode of parenteral administration and the particular site employed, the particular host being treated, and the particular infection being treated. Optimal dosages for a given set of conditions can be readily ascertained by those of skill in the are using conventional dosage determinations or an appropriate adaptation of the experimental data set forth herein.

This invention also relates to a method of treating an active infection in an animal, including humans, wherein said infection is caused by a microorganism which has sterols in its cell membrane, which comprises parenterally administering to such animal a polyene antibiotic liposomal formulation containing a therapeutically effective amount of an aromatic polyene such as candicidin or hamycin. It will be appreciated that the actual preferred amount of a particular aromatic polyene to be given in each dose during the course of treatment of a particular infection will vary according to the variables discussed above.

It will also be appreciated that the optimal course of treatment, i.e., the number of doses of a formulation of this invention given per day for a defined number of days, can be ascertained by those skilled in the art using conventional course of treatment determination tests or an appropriate adaptation of the experimental data set forth herein. Generally, the total daily dose given during the course of treatment will range from 0.6 mg/kg to 5 mg/kg total body weight, depending on a variety of considerations including seriousness of the condition, sensitivity, tolerance, body weight, etc.

The active infections which can be effectively treated by the formulations and methods of this invention include all infections caused by microorganisms containing sterols in their cell membranes, such as yeast, other fungi and other eukaryotic organisms, but does not include any prokaryotic organisms since there organisms lack the requisite sterols in their cell membrane. Of particular interest are infections caused by any species of Candida, such as *Candida albicans, Candida tropicalis*, infections caused by *Torulopsis glabrata* and infections caused by any species of Aspergillus since these infections are pervasive in immunocompromised patients and/or many people in third world countries.

It should be noted that some variability from lot to lot has been observed in the case of hamycin and candicidin. Likely, this is due to the fact that both drugs are not FDA approved drugs, and thus their manufacture is not regulated by FDA specifications. It is therefore advisable that lots of these drugs be checked by one of the foregoing assays to determine their biologic activity.

The foregoing invention has been described in some detail by way of illustration and in terms of examples considered by the inventors to be the preferred methods for practicing the invention. However, it will be appreciated by those of skill in the art that the methods and formulations disclosed herein are in no way meant to be the only modes of practicing this invention. For example, although particular liposomes are preferred, numerous other liposomes and methods for preparing them are known in the art and all are believed to provide benefits in accordance with the invention.

Candicidin was obtained from Dumex Co. (Copenhagen, Denmark) and was encapsulated in liposomes as follows: The lipids Egg phosphatidylcholine (EggPC), dimyristoyl phosphatidylcholine (DMPC), dimyristoyl phosphatidylglycerol (DMPG) dielaidoylphosphatidylcholine (DEPC) phosphatidylthanolamine (PE), dioleolylphosphatidylcholine (DOPC), distearoylphosphatidylcholine (DSPC), dipalmitoylphosphatidylcholine (DPPC) and cholesterol, were obtained from Avanti Polar lipids (Birmingham, Ala).

Candicidin was dissolved in methanol at a concentration of 30 mg/ml, and the candicidin solution was added to the DMPC/cholesterol, the latter two lipids being mixed in a ratio of 9:1. The mixture was placed in a rotary evaporator, until the organic solvents were completely removed. Sterile normal saline was then added and liposomes were obtained by gentle manual agitation. In another experiment, the candicidin solution was added to EggPC/cholesterol, the latter two lipids being mixed in a ratio of 9:1. In a third experiment, the candicidin solution was added to DMPC/DMPG, the latter two lipids being mixed in a ratio of 7:3. In subsequent experiments, the candicidin solution was added to DPPC/PE/cholesterol, or DSPC/PE/cholesterol, or DEPC/PE/cholesterol in a ratio of 6.5:2.5:1 and to DOPC/PE/cholesterol in a ratio of 6:3:1.

In vitro susceptibility testing was performed to compare the activity of free candicidin to that of liposome-encapsulated candicidin. The method of antifungal susceptibility testing used was that described by S. Shadomy in "Manual of Clinical Microbiology" Lennete, E. H., et al. 4th edition. Washington, D.C., American Society for Microbiology. Yeast isolates obtained from patients included *Candida albicans* (10 isolates), *C. tropicalis* (10 isolates) and *Cryptococcus neoformans* (10 isolates). The results of in vitro susceptibility tests clearly showed no difference between the free and all liposomal Candicidin formulations.

The in vitro toxicity liposomal candicidin toward certain mammalian cells was determined. Fresh human red blood cells (RBC) at a final concentration of 20% were added to tubes containing free candicidin solubilized in dimethylformamide. The samples were incubated for 45 minutes at 37° C., centrifuged at 10,000 xg for 20 minutes, and the hemoglobin content of the supernatant determined by its light absorbance. The release of hemoglobin by a hypotonic water solution was also measured and was considered to represent 100% lysis. Results indicated a major decrease of RBC toxicity of candicidin. For example: at 75 Mg/ml, RBC hemolysis went from 75% with the free candicidin down to 10% with DMPC/DMPG—candicidin, 5.4% with DMPC/chol candicidin, 0% with Egg PC—cholesterol, 0% with DOPC—candicidin, 10% with DPPC—candicidin, 11% with DePC—candicidin, and 13% with DSPC —candicidin.

Outbred CF-1 mice (approximately 16 gm from Charles River Lab.) were injected intravenously with $1 \times 10^6$ CFU of *Candida albicans* 336 in saline. *C. albicans* 336 is a human pathogenic isolate obtained from a patient. At 48 hours, a disseminated Candida infection was established in the animal, as documented by both histoplathology and culture of various organs of sacrificed animals. The infected mice were then treated, 48 hours after the *C. albicans* injection, with five daily injections of the maximal tolerated dose (MTD) of one of the following antifungals: Fungizone (commercial amphotericin B, Squibb, N.J.), (2 mg/kg), DMPC/cholesterol—candicidin (5 mg/kg), EggPC/cholesterol candicidin (7.5 mg/kg), DMPC/DMPG—candicidin (2.5 mg/kg), and candicidin in 20% dimethylsulfoxide (DMSO) (1.0 mg/kg). A group of 12 mice was used in each group. Two groups of mice were injected with empty liposomes DMPC/chol, EggPC/cholesterol, and DMPC/DMPG, (same amounts as used in the DMPC/chol/candicidin, DMPC/DMPG candicidin, and EggPC/cholesterol/candicidin). Untreated mice were used as controls. All the control animals, and all of the animals treated with empty liposomes were dead by day 12. Median survival for the treated mice were as follows: 24 days for Fungizone, 28 days for candicidin/DMSO, and $\geq 240$ days for the candicidin liposomal formulation. None of the mice treated with either of the two liposomal formulations had died. The significant improvement in the response rate of disseminated candidiasis may be due to the higher doses of candicidin used. This was made possible by the major decrease in the side effects of this drug when encapsulated with liposome. The MTD of candicidin was increased from 1 mg/kg in the free form to 2.5 mg/kg in the DMPC/DMPG, 5 mg/kg in the DMPC/cholesterol, and $\geq 7.5$ mg/kg in the EggPC/cholesterol formulation.

Small unilamellar vesicles (SUV) were obtained by sonication of the multilamellar vesicles of lysosomal candicidin, for 20 to 30 minutes. After sonication, the SUV were injected intravenously into mice for acute toxicity studies and were compared to candicidin solubilized in dimethylsulphoxide (DMSO). The results showed there was a clear reduction of acute toxicity obtained by incorporation of candicidin into SUV formulations. The maximal tolerated dose of candicidin was increased from 1 mg/kg in the free form to 4.5 mg/kg in the DMPC/cholesterol SUV and more than 6 mg/kg in the EggPC/cholesterol SUV formulation.

References in the following list are incorporated herein in their entirety for the reasons cited.

References

1. Kinsky, S. C., (1962), *Proc. Natl. Acad. Sci. U.S.A.*, 48:1049–1056.
2. Weissman et al., (1967), *J. Biol. Chem.*, 242:616–625.
3. Goth, A., (1978), *Medical Pharmacoloqy, Ninth Edition*, The C. V. Mosby Company, St. Louis, pp. 604–607.

4. Goodman et al., (1975), *The Pharmacological Basis of Therapeutics*, Fifth Edition, MacMiller Publishing Co., Inc., New York, pp. 1235-1238.
5. Drouhet et al., (1987), *Rev. Infect. Diseases*, 9:Supplement, S4-S14.
6. Hamilton-Mill, J. M. T., (1973), *Bacteriol. Reviews*, 37(2):166-196.
7. New et al., (1981), *J. Antimicrob. Chemother.*, Vol. 8 pp. 371-381.
8. Taylor et al., (1982), *Am. Rev. Respir. Dis.*, Vol. 125 pp. 610-611.
9. Graybill et al., (1982), *J. Infect. Dis.*, Vol. 145 pp. 748-752.
10. Tremblay et al., (1983), *Abstr.* 1983 *ICAAC*, No. 755 p. 222.
11. Graybill et al., (1982), *Abstr.* 1982 *ICCAC*, No. 492 p. 152.
12. Lopez-Berestein et al., (1984), *J. Infect. Dis.*, Vol. 120, pp 278-283.
13. Lopez-Berestein et al., (1985), *J. Infect. Dis.*, Vol. 151, pp 704-71.
14. Dutcher, J. D., (1968), *Kirk-Othmer Encyclopedia of Chemical Technology*, 16:133-143.
15. Pansy et al., (1972), *J. Antibiot.*, 25:405-408.
16. Waksman et al., (1965), *Bull. World Health Org.*, 33:219-226.
17. Kirsh et al., U.S. Pat. No. 4,707,470, issued Nov. 17, 1987 (filed May 17, 1985).
18. Grappel et al., (1985), 9th *Int. Congress Int. Soc. Hum. Animal Mycol.*, Atlanta, Ga., May 1985.
19. Singh et al., (1986), *Jrnl. Parenter. Sci. Tech.*, 40:34-42.
20. Dolce et al., (1987), *Clin. Pharmacol. Ther.*, 41:166.
21. Kahn et al., (1987), *Clin. Pharmacol. Ther.*, 41:194.
22. Shadomy et al., (1985), "Laboratory Studies with Antifungal Agents: Susceptibility tests and Bioassays, in *Manual of Clinical Micrology*," Washington, D.C., American Society for Microbiology, pp. 991-999.

Those of skill in the art will recognize that many variations of such embodiments exist. Such variations are intended to be within the scope of the present invention and the appended claims.

What is claimed is:

1. A pharmaceutical formulation comprising a liposome having a therapeutically effective concentration of polyene macrolide antibiotic having an attached p-aminoacetophenone or N-methyl-p-aminoacetophenone substituent.

2. The formulation of claim 1 wherein the polyene macrolide antibiotic is selected from the group consisting of candicidin, hamycin, aurefungin, ascosin, ayfattin, azacolutin, trichomycin, levorin, heptamycin, candimycin, and perimycin.

3. The formulation of claim 1 wherein the polyene macrolide antibiotic is candicidin.

4. The formulation of claim 1 wherein the polyene macrolide antibiotic is hamycin.

5. The formulation of claim 1 or 2 wherein the liposome comprises phospholipids.

6. The formulation of claim 5 wherein the phospholipids are one or more of phosphomonoglyceride, phosphatidic acid and sphingolipid.

7. The formulation of claim 5 wherein the phospholipids are one or more of phosphatidylcholine, phosphatidylserine, phosphatidylglycerol, sphingomyelin and phosphatidic acid.

8. The formulation of claim 5 wherein the phospholipids are one or more of dimyristoylphosphatidylcholine, dimyristoylphosphatidylglycerol, phosphatidylcholine and phosphatidylglycerol.

9. The formulation of claim 5 wherein the phospholipids consist essentially of dimyristoylphosphatidylcholine and dimyristoylphosphatidylglycerol.

10. The formulation of claim 9 wherein the phospholipids are defined further as consisting essentially of dimyristoylphosphatidycholine and dimyristoylphosphatidylglycerol in a ratio of between about 1 to 10 and about 10 to 1.

11. The formulation of claim 9 wherein the phospholipids consist essentially of dimyristoylphosphatidylcholine and dimyristoylphosphatidylglycerol in a ratio of about 7:3.

12. The formulation of claim 1 or 2 wherein the liposome is defined further as being a stable multilamellar vesicle.

13. The formulation of claim 1 or 2 wherein the liposome is defined further as being a small unilammelar vesicle.

14. The formulation of claim 1 or 2 wherein the liposome is defined further as comprising a sterol.

15. The formulation of claim 14 wherein the sterol is cholesterol.

16. A method for treating disseminated fungal infection in an animal comprising administering to an animal a pharmaceutical formulation comprising a liposome having a therapeutically effective amount of a polyene macrolide antibiotic having an attached p-aminoacetophenone or N-methyl-p-aminoacetophenone substituent.

17. The method of claim 16 or 41 wherein the liposome comprises phospholipids.

18. The method of claim 17 wherein the phospholipids are one or more of phosphomonoglyceride, phosphatidic acid and sphingolipid.

19. The method of claim 17 wherein the phospholipids are one or more of phosphatidylcholine, phosphatidylserine, phosphatidylglycerol, sphingomyelin, phosphatidic acid, egg phosphatidylcholine, and phosphatidylethanolamine.

20. The method of claim 17 wherein the phospholipids are one or more of dimyristoylphosphatidylcholine, dimyristoylphosphatidylglycerol, dielaidoylphosphatidylcholine, dioleoylphosphatidylcholine, distearyloylphosphatidylcholine and dipalmitoylphosphatidylcholine.

21. The method of claim 20 wherein the liposome comprises cholesterol.

22. The method of claim 16 or 41 wherein the administering is parenteral.

23. The method of claim 16 or 41 wherein the animal is a human.

24. The method of claim 16 or 41 wherein the therapeutically effective amount is between about 1 mg/kg body weight and about 10 mg/kg body weight.

25. The method of claim 16 or 41 wherein the therapeutically effective amount is between about 2.5 mg/kg body weight and about 6 mg/kg body weight.

26. The method of claim 17 wherein the phospholipids consist essentially of dimyristoylphosphatidylcholine and dimyristoylphosphatidylglycerol.

27. The method of claim 26 wherein the dimyristoylphosphatidylcholine and dimyristoylphosphatidylglycerol are in a ratio of about 7 to 3.

28. The method of claim 16 or 41 wherein the administration is intravenous, intraarterial, subcutaneous, intramuscular, intralymphatic, intraperitoneal or intrapleural.

29. The method of claim 16 or 41 wherein the liposome is multilamellar.

30. The method of claim 16 or 41 wherein the liposome is unilamellar.

31. A method for the treatment of an infection in an animal caused by a microorganism which has sterols in its membrane, the treatment method comprising parenterally administering to such an animal a liposome containing a polyene macrolide antibiotic having an attached p-aminoacetophenone or N-methyl-p-aminoacetophenone substituent, in a therapeutically effective amount.

32. The method of claim 31 or 42 wherein the microorganism is one or more of *C. albicans, C. tropicalis, C. neoformans*, aspergillus, cryptococcus, zycomycetes, fusarium, and trichosporon.

33. The formulation of claim 1 wherein the therapeutically effective concentration is between about 100 ug(microgram)/ml and about 2.0mg/ml.

34. A method for treating disseminated fungal infection in an animal comprising administering to an animal a pharmaceutical formulation comprising a liposome having a therapeutically effective amount of a polyene macrolide antibiotic selected from the group consisting of candicidin, hamycin, aurefungin, ascosin, ayfattin, azacolutin, trichomycin, levorin, heptamycin, candimycin, and perimycin.

35. A method for the treatment of an infection in an animal caused by a microorganism which has sterols in its membrane, the treatment method comprising parenterally administering to such an animal a liposome comprising a therapeutically effective amount of a polyene macrolide antibiotic selected from the group consisting of candicidin, hamycin, aurefungin, ascosin, ayfattin, azacolutin, trichomycin, levorin, heptamycin, candimycin, and perimycin.

* * * * *

UNITED STATES PATENT AND TRADEMARK OFFICE
CERTIFICATE OF CORRECTION

PATENT NO. : 4,999,199

DATED : March 12, 1991

INVENTOR(S) : Anaissie et al

It is certified that error appears in the above-identified patent and that said Letters Patent is hereby corrected as shown below:

In claim 22, column 10, line 53 delete the term "41" and replace it with the term --34--.

In claim 23, column 10, line 55 delete the term "41" and replace it with the term --34--.

In claim 24, column 10, line 57 delete the term "41" and replace it with the term --34--.

In claim 25, column 10, line 60 delete the term "41" and replace it with the term --34--.

In claim 28, column 11, line 1 delete the term "41" and replace it with the term --34--.

In claim 29, column 11, line 5 delete the term "41" and replace it with the term --34--.

In claim 30, column 11, line 7 delete the term "41" and replace it with the term --34--.

UNITED STATES PATENT AND TRADEMARK OFFICE
CERTIFICATE OF CORRECTION

PATENT NO. : 4,999,199

DATED : March 12, 1991

INVENTOR(S) : Anaissie et al

It is certified that error appears in the above-identified patent and that said Letters Patent is hereby corrected as shown below:

In claim 32, column 11, line 18 delete the term "42" and replace it with the term --35--.

Signed and Sealed this

Twentieth Day of October, 1992

Attest:

DOUGLAS B. COMER

Attesting Officer       Acting Commissioner of Patents and Trademarks